United States Patent [19]

Bierman

[11] Patent Number: 5,192,274
[45] Date of Patent: Mar. 9, 1993

[54] ANCHOR PAD FOR CATHETERIZATION SYSTEM

[76] Inventor: Steven F. Bierman, 143 Eighth St., Del Mar, Calif. 92014

[21] Appl. No.: 697,640

[22] Filed: May 8, 1991

[51] Int. Cl.⁵ ............................................. A61M 5/32
[52] U.S. Cl. ................................................... 604/180
[58] Field of Search ............... 604/174, 177, 178, 179, 604/180; 128/DIG. 26

[56] References Cited

U.S. PATENT DOCUMENTS

| | | |
|---|---|---|
| 747,360 | 12/1903 | Barry . |
| 2,525,398 | 10/1950 | Collins . |
| 2,533,961 | 12/1950 | Rouseau et al. . |
| 3,064,648 | 11/1962 | Bujan . |
| 3,167,072 | 1/1965 | Stone et al. . |
| 3,394,954 | 7/1968 | Sarns . |
| 3,686,896 | 8/1972 | Rutter . |
| 3,766,915 | 10/1973 | Rychlik . |
| 3,900,026 | 8/1975 | Wagner . |
| 3,906,946 | 9/1975 | Nordstrom . |
| 3,920,001 | 11/1975 | Edwards . |
| 3,973,565 | 8/1976 | Steer . |
| 4,037,599 | 7/1977 | Raulerson . |
| 4,082,094 | 4/1978 | Dailey . |
| 4,084,911 | 4/1978 | DeWitt . |
| 4,099,744 | 7/1978 | Kutnyak et al. . |
| 4,114,618 | 9/1978 | Vargas . |
| 4,116,196 | 9/1978 | Kaplan et al. . |
| 4,123,091 | 10/1978 | Cosentino et al. . |
| 4,129,128 | 12/1978 | McFarlane . |
| 4,133,312 | 1/1979 | Burd . |
| 4,161,177 | 7/1979 | Fuchs . |
| 4,224,937 | 9/1980 | Gordon ............................... 604/180 |
| 4,250,880 | 2/1981 | Gordon . |
| 4,316,461 | 2/1982 | Marais et al. . |
| 4,326,519 | 4/1982 | D'Alo et al. . |
| 4,362,156 | 12/1982 | Feller, Jr. et al. . |
| 4,392,853 | 7/1983 | Muto . |
| 4,405,163 | 9/1983 | Voges et al. . |
| 4,449,975 | 5/1984 | Perry . |
| 4,474,559 | 10/1984 | Steiger . |
| 4,516,968 | 5/1985 | Marshall et al. . |
| 4,585,435 | 4/1986 | Vaillancourt . |
| 4,711,636 | 12/1987 | Bierman . |
| 4,742,824 | 5/1988 | Payton et al. ....................... 604/174 |
| 4,752,292 | 6/1988 | Lopez et al. . |
| 4,792,163 | 12/1988 | Kulle . |
| 4,838,858 | 6/1989 | Wortham et al. . |
| 4,863,432 | 9/1989 | Kvalo . |
| 4,880,412 | 11/1989 | Weiss . |
| 4,897,082 | 1/1990 | Erskine ............................... 604/180 |
| 4,966,582 | 10/1990 | Sit et al. . |
| 4,976,700 | 12/1990 | Tollini ................................ 604/180 |
| 4,981,469 | 1/1991 | Whitehouse et al. . |
| 4,997,421 | 3/1991 | Palsrok et al. . |
| 5,037,397 | 8/1991 | Kalt et al. ........................... 604/180 |

FOREIGN PATENT DOCUMENTS 2341297 4/1975 European Pat. Off. .
0263789 9/1986 Fed. Rep. of Germany .

Primary Examiner—Gene Mancene
Assistant Examiner—Thomas Price
Attorney, Agent, or Firm—Knobbe, Martens, Olson & Bear

[57] ABSTRACT

An anchor pad is disclosed having a self-adhesive material applied to one surface of the pad and one or more barbed uprights extending from the opposite surface of the pad in order to securely engage the suture holes of a central line catheter. The barbs permit slidable engagement with the catheter but prevent disengagement. In order to remove the catheter, the barbs can be easily snipped or cut.

10 Claims, 1 Drawing Sheet

ANCHOR PAD FOR CATHETERIZATION SYSTEM

BACKGROUND OF THE INVENTION

1. Field of the Invention

The present invention relates to an anchor pad for an intravenous catheterization connector, and, more particularly, to an anchor pad for use with a triple-lumen connector.

2. Description of the Related Art

It is very common in the treatment of patients to utilize intravenous ("IV") catheters to introduce fluids and medications directly into the bloodstream. In many cases, and particularly with respect to cardiac therapy, the IV catheter is introduced into a central line or a larger vein located close to the patient's heart. In such circumstances, long term infusion typically requires that the catheter remain in place for many days. In order to secure such a central line IV catheter in position at the injection site, the IV tubing is commonly mounted on a thin flexible pad or seat which is then sutured to the patient's skin. This combination of tubing and pad comprises a connector to which one or more other IV supply lines having compatible connectors can be attached. In one example, a triple-lumen connector sold under the brand name ARROW ® provides three separate supply lines for secondary IV fluids or manual injection sites.

A number of problems, however, have arisen with respect to such central line connectors such as the triple-lumen connector described above. First, suturing the pad to the patient's skin is painful. Also, with the passage of time, the sutures frequently tear through the soft plastic material comprising the seat of the connector, thus permitting movement of the connector in the injection site and adding to the pain and discomfort of the patient. Even if they do not tear, the sutures may loosen to such an extent that 2 to 3 mm of movement occurs in and out of the injection site. This movement is not only painful to the patient, but also fosters bacteria infections at the site. It is estimated that there are approximately 50,000 catheter infections per year, many of which are due to problems such as those described above.

Thus, there is a need for a more secure means for attachment of a central line catheter to the body of the patient at the injection site.

SUMMARY OF THE INVENTION

The present invention comprises an anchor pad which securely fastens onto the body of the patient by means of an adhesive applied to one planar side of the pad. The opposite planar side of the pad includes one or more barbed uprights which engage the suture holes commonly found in typical central line connectors, such as the triple-lumen connector described above. In the preferred embodiment, the barbed uprights correspond to the number, size and spacing of the connector suture holes.

The triple-lumen connector mounts on the anchor pad of the present invention by aligning the suture holes in the plastic seat of the connector over the barbed uprights on the anchor pad. The connector is then pressed down over the barbs until the connector is secure. The configuration of the barbs permits movement of the connector toward the body of the patient but prevents movement in the opposite direction, thus preventing accidental disengagement.

When it is necessary or desirable to remove the central line connector, the barbs can be easily and quickly snipped off above the connector to allow the connector to lift off of the barbed stumps away from the patient. Thus, the pain and discomfort associated with such central line catheters is avoided, while at the same time providing a secure connection.

DETAILED DESCRIPTION OF THE INVENTION

Figure 1:
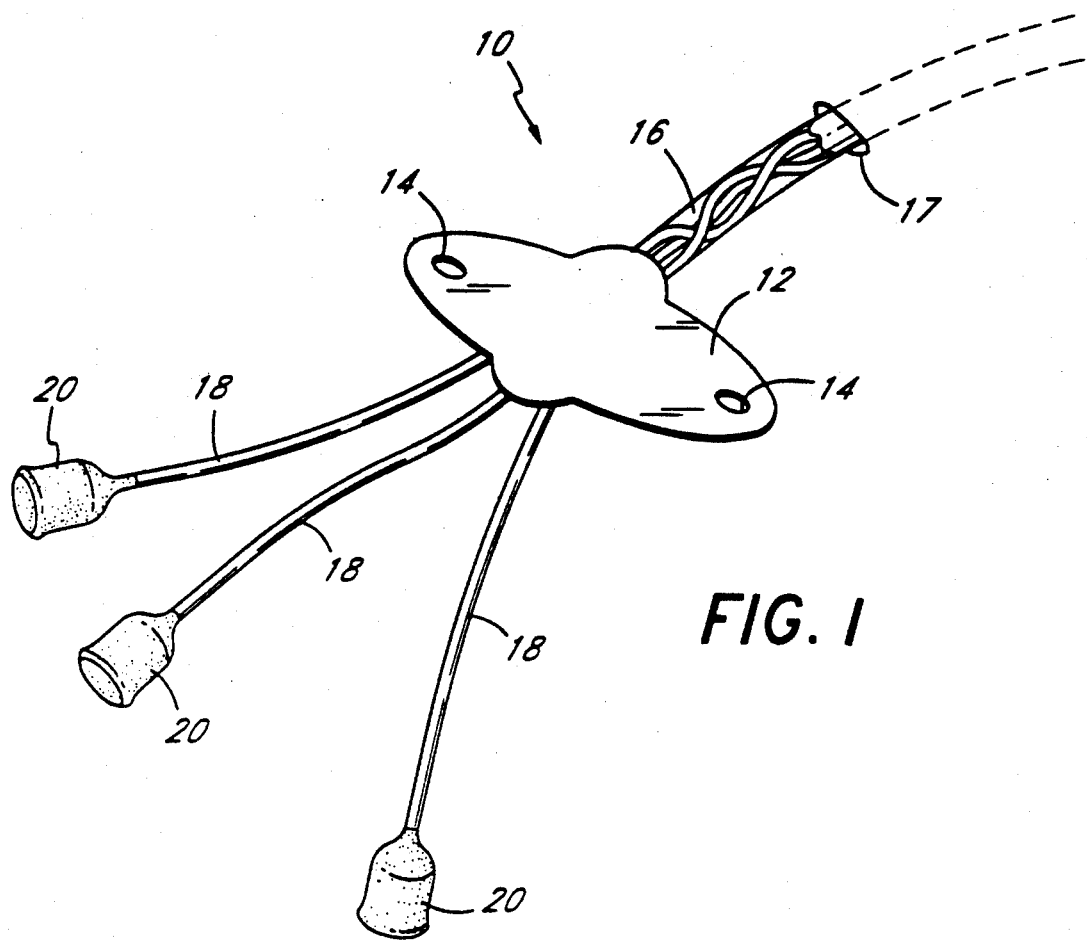
FIG. 1 is a perspective view of a typical triple-lumen central line catheter having a seat with a pair of suture holes formed therein.

Referring to FIG. 1, there is shown a typical triple-lumen central line catheter 10 of the type manufactured under the ARROW ® brand name. Although the present invention is illustrated and described herein in connection with a triple-lumen catheter, it should be understood that the principles of the invention apply equally well to other types of catheters with various configurations.

The triple-lumen catheter 10 of FIG. 1 comprises a central planar seat 12 formed of a soft pliable plastic, having a pair of suture holes 14 formed therein. Extending away from the seat in one direction is a cannula 16 which inserts into the injection site 17 in the body of the patient, in accordance with standard catheterization procedures. Extending away from the seat in the opposite direction are three lengths of IV tubing 18, each ending in a standard IV connector 20, such as, for example, a lure-type lock or septum cap. These standard IV connectors 20 can receive compatible connectors (not shown) formed on the end of IV supply tubing, or can receive manual injections for administering medication or other fluids directly into a central vein of the patient.

In order to secure the triple-lumen catheter 10 at the injection site, the seat 12 is typically positioned on the body and sutured to the skin of the patient by means of the suture holes 14. Over time, however, as explained above, the sutures either loosen or tear completely through the seat material. The patient experiences pain and discomfort, and risks infection as a result.

Figure 2:
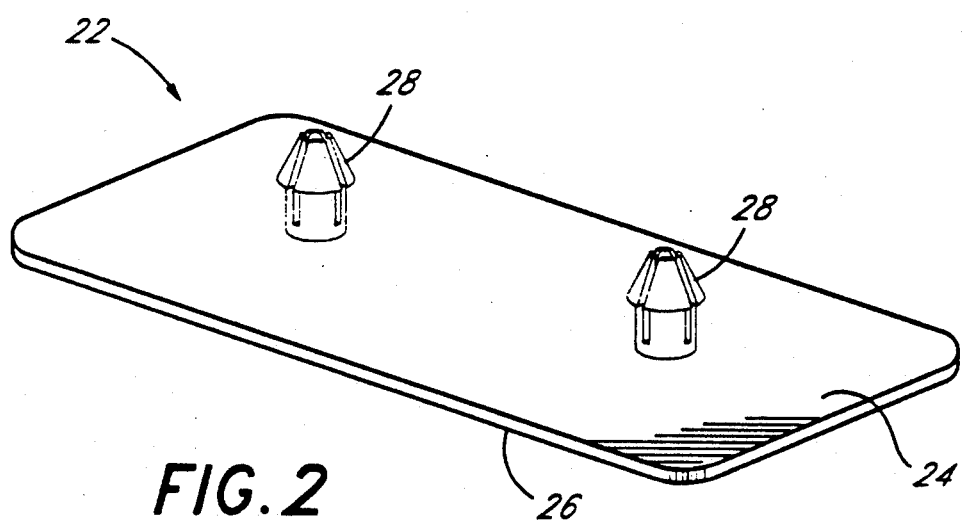
FIG. 2 is a perspective view of the anchor pad of the present invention illustrating a pair of upstanding barbs to receive the suture holes of the connector.

Referring to FIG. 2, there is shown the anchor pad 22 of the present invention comprising a planar pad 24 having a self-adhesive material applied to the bottom surface 26 thereof. The adhesive secures the anchor pad 22 to the patient's body without sutures.

A pair of barbed uprights 28 integrally mount on the opposite side of the pad 24. The barbs 28 are spaced and configured to receive the suture holes 14 on the seat 12 of the triple-lumen catheter 10 (shown in FIG. 1). In addition, the diameter of the cylindrical portion of the uprights (not including the barbs) is sized to slightly deform the seat of the connector as it press fits onto the pad. Preferably, the seat deforms elastically to be securely retained on the anchor pad.

It will be noted that the barbs 28 elastically permit the seat 12 to pass down over the jagged edges of the barbs, but prevent movement of the seat in the opposite direction. Thus, the anchor pad of the present invention securely mounts the seat of the triple-lumen catheter on the patient's body. Not only is the patient relieved of pain, but the risk of complete or partial disengagement is eliminated.

In order to remove the catheter, the barbs are simply snipped off so that the seat can be easily lifted over the remaining stumps. The pad is then removed from the patient with minimal discomfort. The barbs are constructed from a material which is less elastic than the material comprising the connector seat but which is easily severable.

Therefore, the anchor pad of the present invention presents a significant advance in the use and attachment of central line catheters. While the preferred arrangement of the present invention has been illustrated and described, it should be understood that various changes and modifications to the system illustrated will readily come to mind which fall within the scope of the invention as set forth in the appended claims.

What is claimed is:

1. An anchoring system for securing a catheter to the body of a patient comprising:
    a catheter connector comprising a substantially planar seat having at least one suture hole formed therein; and
    an anchoring apparatus comprising:
        an adhesive member for secure attachment to the body of the patient; and
        at least one retention member mounted on said adhesive member, said retention member being configured to insert through said suture hole of said catheter seat and to engage with the catheter seat about the suture hole to prevent accidental disengagement of said catheter from said adhesive member, whereby the catheter seat is attached to the adhesive member.

2. An anchoring apparatus for securing a catheter to the body of a patient wherein said catheter is provided with a substantially planar seat having suture holes formed therein, the apparatus comprising:
    an adhesive member for secure attachment to the body of the patient; and
    at least one retention member mounted on said adhesive member spaced and configured to correspond with at last one of said suture holes for receiving said seat of said catheter in slidable engagement, said retention member preventing accidental disengagement of said catheter, wherein said retention member is barbed, permitting the planar seat of the catheter to move relative to said retention member in one direction only.

3. The apparatus of claim 2, wherein said apparatus includes a plurality of barbed retention members positioned on said adhesive member so as to be in alignment with said suture holes.

4. The apparatus of claim 1, wherein the diameter of said retention member is slightly larger than that of said suture hole.

5. A method for attaching an intravenous catheterizaton connector to a body of a patient, wherein the catheterization connector including a substantially planar seat having suture holes formed therein, said method comprising the steps of:
    providing an anchoring apparatus having an adhesive member and at least one retention member, said retention member extending outwardly from said adhesive member;
    placing said adhesive member on said patient body to secure said anchoring apparatus thereon with said retention member extending away from said patient body; and
    inserting said retention member through a suture hole of the catheterization connector planar seat to prevent unintentional disengagement between the retention member and the planar seat of the intravenous catheterization connector.

6. A method for attaching an intravenous catheterization connector to a body of a patient, comprising the steps of:
    providing an anchoring apparatus having an adhesive member and at least one retention member, said retention member extending outwardly from said adhesive member;
    configuring said retention member with a plurality of barbs radially extending towards said adhesive member acute to a longitudinal axis of the retention member;
    placing said adhesive member on said patient body to secure said anchoring apparatus thereon with said retention member extending away from said patient body; and
    coupling said intravenous catheterization connector with said retention member in a manner preventing unintentional disengagement between the retention member and the intravenous catheterization connector by inserting said retention member into a hole of said intravenous catheterization connector by elastically deforming said barbs to permit said retention member to insert into said hole but to prevent said retention member from extracting from said hole.

7. The method of claim 6, additionally comprising the steps of:
    providing a plurality of retention members corresponding to the number of holes in said intravenous catheterization connector;
    positioning said retention members on said anchoring apparatus such that each retention member position corresponds with a hole position of said intravenous catheterization connector.

8. A method for attaching an intravenous catheterization connector to a body of a patient, comprising the steps of:
    providing an anchoring apparatus having an adhesive member and at least one retention member, said retention member extending outwardly from said adhesive member;
    placing said adhesive member on said patient body to secure said anchoring apparatus thereon with said retention member extending away from said patient body;
    coupling said intravenous catheterization connector with said retention member in a manner preventing unintentional disengagement between the retention member and the intravenous catheterization connector; and
    severing the retention member between said adhesive member and said connector to permit disengagement between said connector and said adhesive member.

9. An anchoring apparatus for securing a catheterization connector to the body of a patient, wherein said catheterization connector comprises a substantially planar seat having suture holes formed therein, said anchoring apparatus comprising:
    an adhesive member for secure attachment to the body of the patient; and a plurality of retention members mounted on said adhesive member, said retention members being spaced apart from one another such that the spacing between a plurality of retention members correspond with the spacing between a corresponding plurality of suture holes of the connector seat, whereby the connector seat is attached to said adhesive member by inserting said retention members through the corresponding suture hole.

10. An anchoring apparatus for securing a catheterization connector to the body of a patient, wherein said catheterization connector comprises a substantially planar seat having suture holes formed therein, said anchoring apparatus comprising:

an adhesive member for secure attachment to the body of the patient; and at least one retention member mounted on said adhesive member and configured to insert through a corresponding suture hole of the connector seat and to engage with the connector seat about the suture hole to prevent accidental disengagement of the catheterization connector from said adhesive member, whereby the connector seat is attached to the adhesive member.

* * * * *